(12) United States Patent
Bosch et al.

(10) Patent No.: US 7,998,507 B2
(45) Date of Patent: *Aug. 16, 2011

(54) NANOPARTICULATE COMPOSITIONS OF MITOGEN-ACTIVATED PROTEIN (MAP) KINASE INHIBITORS

(75) Inventors: H. William Bosch, Bryn Mawr, PA (US); Greta G. Cary, Landsdale, PA (US); Douglas C. Hovey, Gilbertsville, PA (US); Rajeev A. Jain, Framingham, MA (US); Laura J. Kline, Harleysville, PA (US); Elaine Merisko-Liversidge, West Chester, PA (US); Kevin D. Ostrander, Ringoes, NJ (US); Niels P. Ryde, Malvern, PA (US); Stephen B. Ruddy, Schwenksville, PA (US)

(73) Assignee: Elan Pharma International Ltd., Athlone, County Westmeath (IE)

( * ) Notice: Subject to any disclaimer, the term of this patent is extended or adjusted under 35 U.S.C. 154(b) by 1068 days.
This patent is subject to a terminal disclaimer.

(21) Appl. No.: 11/275,069

(22) Filed: Dec. 7, 2005

(65) Prior Publication Data

US 2006/0193920 A1     Aug. 31, 2006

Related U.S. Application Data

(63) Continuation-in-part of application No. 10/323,736, filed on Dec. 20, 2002, now Pat. No. 7,198,795, which is a continuation-in-part of application No. 10/075,443, filed on Feb. 15, 2002, now Pat. No. 6,592,903, which is a continuation of application No. 09/666,539, filed on Sep. 21, 2000, now Pat. No. 6,375,986, application No. 11/275,069, which is a continuation-in-part of application No. 10/392,303, filed on Mar. 20, 2003, now abandoned.

(60) Provisional application No. 60/365,524, filed on Mar. 20, 2002.

(51) Int. Cl.
*A61K 9/14* (2006.01)
*A61K 9/00* (2006.01)
*A61K 31/66* (2006.01)
*A61K 31/385* (2006.01)
*A61K 31/522* (2006.01)
*A61K 31/525* (2006.01)
*A61K 31/557* (2006.01)
*A61K 36/82* (2006.01)
*A61K 36/328* (2006.01)
*A61K 36/886* (2006.01)
*A61K 38/17* (2006.01)
*A61K 48/00* (2006.01)

(52) U.S. Cl. ........ 424/489; 424/729; 424/744; 424/748; 424/768; 424/776; 514/12.1; 514/102; 514/251; 514/263.31; 514/440; 514/561; 514/573

(58) Field of Classification Search ........................ None
See application file for complete search history.

(56) References Cited

U.S. PATENT DOCUMENTS 4,657,901 A    4/1987    Ueda et al.
(Continued)

FOREIGN PATENT DOCUMENTS

EP    0 275 796 B2    9/1995
(Continued)

OTHER PUBLICATIONS

Cobb et al., "MAP Kinase Signaling Pathways," *Promega Notes Magazine* (1996), No. 59, p. 37, http://www.promega.com/pnotes/59/5644f/5644f.html.

(Continued)

*Primary Examiner* — Ernst Arnold
*Assistant Examiner* — Christopher R Lea
(74) *Attorney, Agent, or Firm* — Foley & Lardner LLP

(57) ABSTRACT

Nanoparticulate compositions comprising at least one poorly soluble MAP kinase inhibitor and at least one surface stabilizer are described. The nanoparticulate compositions have an average particle size of less than about 2000 nm. The invention also describes methods of making and using such compositions.

35 Claims, 1 Drawing Sheet

U.S. PATENT DOCUMENTS

| | | | |
|---|---|---|---|
| 4,783,484 A | 11/1988 | Violante et al. | |
| 4,826,689 A | 5/1989 | Violanto et al. | |
| 4,997,454 A | 3/1991 | Violante et al. | |
| 5,024,843 A | 6/1991 | Kuczynski et al. | |
| 5,118,528 A | 6/1992 | Fessi et al. | |
| 5,145,684 A * | 9/1992 | Liversidge et al. | 424/489 |
| 5,298,262 A | 3/1994 | Na et al. | |
| 5,302,401 A | 4/1994 | Liversidge et al. | |
| 5,318,767 A | 6/1994 | Liversidge et al. | |
| 5,326,552 A | 7/1994 | Na et al. | |
| 5,328,404 A | 7/1994 | Bacon | |
| 5,336,507 A | 8/1994 | Na et al. | |
| 5,340,564 A | 8/1994 | Illig et al. | |
| 5,346,702 A | 9/1994 | Na et al. | |
| 5,349,957 A | 9/1994 | Yudelson | |
| 5,352,459 A | 10/1994 | Hollister et al. | |
| 5,399,363 A | 3/1995 | Liversidge et al. | |
| 5,401,492 A | 3/1995 | Kellar et al. | |
| 5,429,824 A | 7/1995 | June | |
| 5,447,710 A | 9/1995 | Na et al. | |
| 5,451,393 A | 9/1995 | Liversidge et al. | |
| 5,466,433 A | 11/1995 | Bacon et al. | |
| 5,466,440 A | 11/1995 | Ruddy et al. | |
| 5,470,583 A | 11/1995 | Na et al. | |
| 5,472,683 A | 12/1995 | Illig | |
| 5,494,683 A | 2/1996 | Liversidge et al. | |
| 5,500,204 A | 3/1996 | Osifo | |
| 5,503,723 A | 4/1996 | Ruddy et al. | |
| 5,510,118 A | 4/1996 | Bosch et al. | |
| 5,518,187 A | 5/1996 | Bruno et al. | |
| 5,518,738 A | 5/1996 | Eickhoff et al. | |
| 5,521,218 A | 5/1996 | Osifo | |
| 5,525,328 A | 6/1996 | Bacon et al. | |
| 5,534,270 A | 7/1996 | De Castro | |
| 5,543,133 A | 8/1996 | Swanson et al. | |
| 5,552,160 A | 9/1996 | Liversidge et al. | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,749 A | 11/1996 | Illig | |
| 5,573,750 A | 11/1996 | Singh | |
| 5,573,783 A | 11/1996 | Desieno et al. | |
| 5,580,579 A | 12/1996 | Ruddy et al. | |
| 5,585,108 A | 12/1996 | Ruddy et al. | |
| 5,587,143 A | 12/1996 | Wong | |
| 5,591,456 A | 1/1997 | Franson et al. | |
| 5,593,657 A | 1/1997 | Ruddy et al. | |
| 5,603,916 A | 2/1997 | Singh | |
| 5,622,938 A | 4/1997 | Wong | |
| 5,628,981 A | 5/1997 | Liversidge et al. | |
| 5,643,552 A | 7/1997 | Illig | |
| 5,662,883 A | 9/1997 | Bagchi et al. | |
| 5,665,330 A | 9/1997 | Wong | |
| 5,665,331 A | 9/1997 | Bagchi et al. | |
| 5,668,196 A | 9/1997 | Robinson et al. | |
| 5,670,136 A | 9/1997 | Bacon et al. | |
| 5,716,642 A | 2/1998 | Bagchi et al. | |
| 5,718,388 A | 2/1998 | Czekai et al. | |
| 5,718,919 A | 2/1998 | Ruddy et al. | |
| 5,741,522 A | 4/1998 | Violante et al. | |
| 5,747,001 A | 5/1998 | Wiedmann et al. | |
| 5,776,496 A | 7/1998 | Violante et al. | |
| 5,834,025 A | 11/1998 | De Garavilla et al. | |
| 5,862,999 A | 1/1999 | Czekai et al. | |
| 6,045,829 A | 4/2000 | Liversidge et al. | |
| 6,068,858 A | 5/2000 | Liversidge et al. | |
| 6,117,455 A | 9/2000 | Takada et al. | |
| 6,153,225 A | 11/2000 | Lee et al. | |
| 6,165,506 A | 12/2000 | Jain et al. | |
| 6,221,400 B1 | 4/2001 | Liversidge et al. | |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,316,029 B1 | 11/2001 | Jain et al. | |
| 6,375,986 B1 | 4/2002 | Ryde et al. | |
| 6,383,471 B1 | 5/2002 | Chen et al. | |
| 6,428,814 B1 | 8/2002 | Bosch | |
| 6,431,478 B1 | 8/2002 | Reed et al. | |
| 6,432,381 B2 | 8/2002 | Liversidge et al. | |
| 6,592,903 B2 * | 7/2003 | Ryde et al. | 424/489 |
| 2002/0012675 A1 | 1/2002 | Jain et al. | |

FOREIGN PATENT DOCUMENTS

| | | |
|---|---|---|
| EP | 0 499 299 A2 | 8/2002 |
| JP | 9-271658 | 10/1997 |
| WO | WO 96/25918 | 8/1996 |
| WO | WO 98/07414 A1 | 2/1998 |
| WO | WO 9827098 A1 * | 6/1998 |
| WO | WO 98/35666 | 8/1998 |
| WO | WO 98/51825 A1 | 11/1998 |
| WO | WO 00/12124 A1 | 3/2000 |
| WO | WO 00/18374 | 4/2000 |
| WO | WO 00/18374 A1 | 4/2000 |
| WO | WO 00/23072 A1 | 4/2000 |
| WO | WO 00/27363 | 5/2000 |
| WO | WO 01/17546 A1 | 3/2001 |
| WO | WO 02/098565 A1 | 12/2002 |

OTHER PUBLICATIONS

Hoshino et al., "Constitute activation of the 41-/43-kDa mitogen-activated protein kinase signaling pathway in human tumors," *Oncogene* (1998), vol. 18, pp. 813-822.

Sebolt-Leopold et al., "Blockade of the MAP kinase pathway suppresses growth of colon tumors in vivo," *Nature Medicine* (Jul. 1999), vol. 5, No. 7, pp. 810-816.

Jiang et al., Characterization of the Structure and Function of a New Mitogen-activated Protein Kinase (p38β), *The Journal of Biological Chemistry* (1996), vol. 271, No. 30, pp. 17920-17926.

Frantz et al., "The Activation State of p38 Mitogen-Activated Protein Kinase Determines the Efficiency of ATP Competition for Pyridinylimidazole Inhibitor Binding," *Biochemistry* (1998), vol. 37, pp. 13846-13853.

Nemoto et al., "Induction of Apoptosis by SB202190 through Inhibition of p38β Mitogen-activated Protein Kinase," *The Journal of Biological Chemistry* (1998), vol. 273, No. 26, pp. 16415-16420.

Davies et al., "Specificity and mechanism of action of some commonly used protein kinase inhibitors," *Biochem J.* (2000), vol. 351, pp. 95-105.

www.Tocris.com, SB 202190, 2006.

Notice of Rejections from related Japanese Patent Application No. 2003-577854 dated Sep. 14, 2009.

* cited by examiner

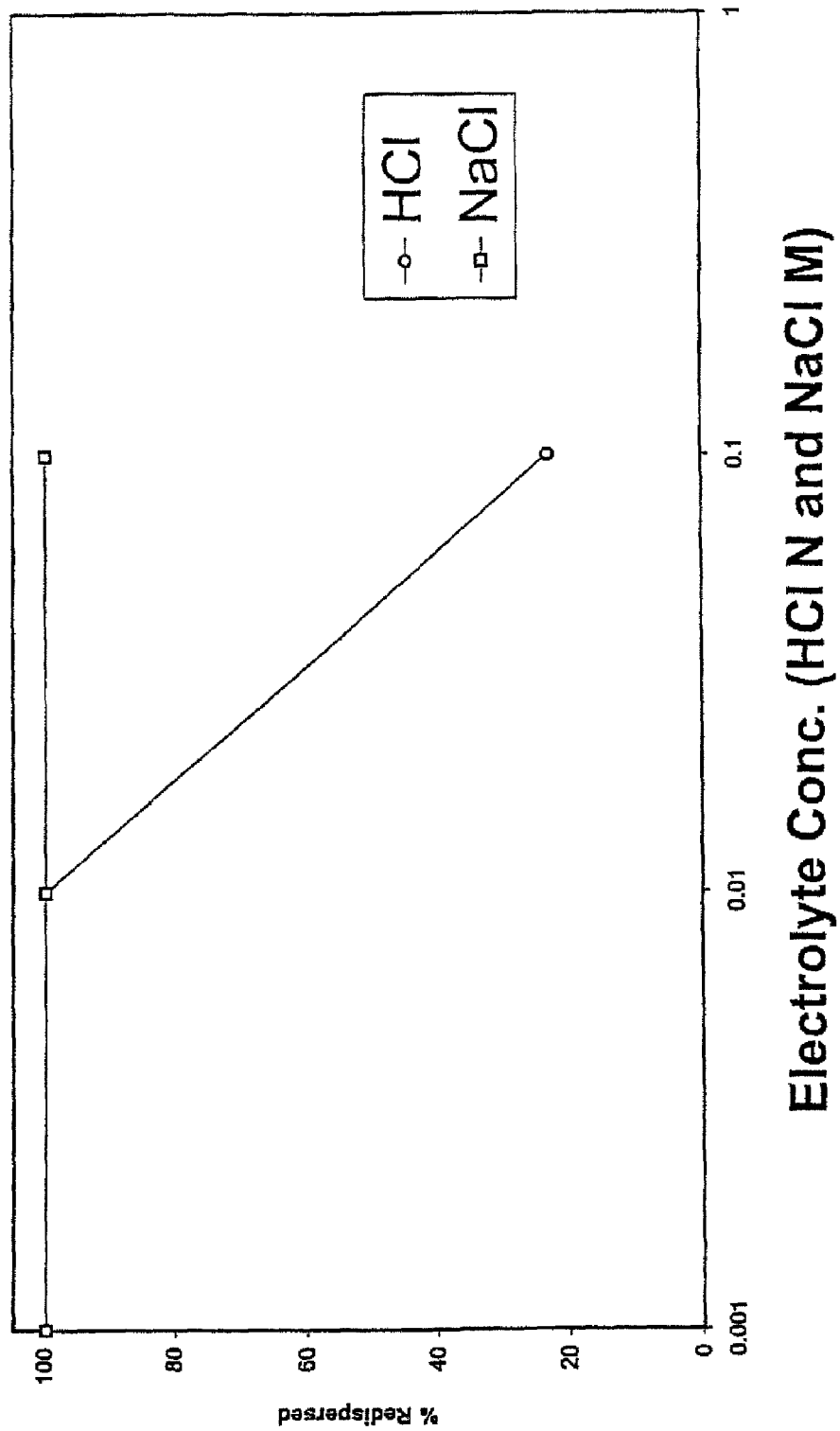

NANOPARTICULATE COMPOSITIONS OF MITOGEN-ACTIVATED PROTEIN (MAP) KINASE INHIBITORS

CROSS REFERENCE TO THE RELATED APPLICATIONS

The present application is a continuation-in-part of U.S. patent application Ser. No. 10/392,303, filed on Mar. 20, 2003, now abandoned, which claims benefit under 35 U.S.C. §119(e) to U.S. Provisional Patent Application No. 60/365,524, filed on Mar. 20, 2002. The present application also is a continuation-in-part of U.S. patent application Ser. No. 10/323,736, filed on Dec. 20, 2002, now U.S. Pat. No. 7,198,795, which is a continuation-in-part of U.S. patent application Ser. No. 10/075,443, filed on Feb. 15, 2002, now U.S. Pat. No. 6,592,903, which is a continuation of U.S. patent application Ser. No. 09/666,539, filed on Sep. 21, 2000, now U.S. Pat. No. 6,375,986.

FIELD OF THE INVENTION

The present invention is directed to nanoparticulate formulations of Mitogen-Activated Protein (MAP) kinase inhibitors and methods of making and using such compositions.

BACKGROUND OF THE INVENTION

A. Background Regarding Nanoparticulate Compositions

Nanoparticulate compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. This invention is an improvement over that disclosed in the '684 patent, as the '684 patent does not describe nanoparticulate compositions comprising a MAP kinase inhibitor.

The '684 patent describes a method of screening active agents to identify useful surface stabilizers that enable the production of a nanoparticulate composition. Not all surface stabilizers will function to produce a stable, non-agglomerated nanoparticulate composition for all active agents.

Methods of making nanoparticulate compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described in, for example, U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate," U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

Amorphous small particle compositions are described in, for example, U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

B. Background Regarding MAP kinase Inhibitors

MAP kinase is the generic term used to describe a family of serine/threonine kinases. MAP kinases, also referred to as extracellular signal-regulated protein kinases or ERKs, are the terminal enzymes in a three-kinase cascade. The reiteration of three-kinase cascades for related but distinct signaling pathways gave rise to the concept of a MAPK pathway as a modular, multifunctional signaling element that acts sequentially within one pathway, where each enzyme phosphorylates and thereby activates the next member in the sequence. A canonical MAPK module thus consists of three protein kinases: a MAPK kinase (or MEKK) that activates a MAPK kinase (or MEK) which, in turn, activates a MAPK/ERK enzyme.

Each of the MAPK/ERK, JNK (c-jun amino terminal protein kinase (or SAPK)), and p38 cascades consists of a three-enzyme module that includes MEKK, MEK, and an ERK or MAPK superfamily member. A variety of extracellular signals trigger initial events upon association with their respective cell surface receptors and this signal is then transmitted to the interior of the cell where it activates the appropriate cascades.

Below is provided a summary of enzymes involved in MAP kinase signaling pathways. See Cobb et al., "MAP Kinase Signaling Pathways," *Promega Note,* 59:37 (1996); and http://www.promega.com/pnotes/59/5644f/5644f.html. At present, the three most characterized MAP kinase families are the extracellular regulated kinases 1 and 2 (ERK1/2), the c-jun N-terminal kinases 46 and 54 (JNK46/JNK54), and the p38 kinases.

Enzymes Involved in MAP Kinase Signaling Pathways
Generic Pathway
MAPK Mitogen-activated protein kinase (or ERK) superfamily; has TXY consensus sequence in the catalytic core. ERK1/2, p38HOG, and JNK/SAPK represent related yet distinct terminal enzymes in parallel pathways.
ERK Extracellular signal-regulated protein kinase (or MAPK).
MEK MAPK (ERK) kinase; Ser/Thr/Tyr-specific protein kinase that activates MAPKs by phosphorylating both Thr and Tyr within the TXY consensus sequence.
MEKK MEK kinase or MAPK kinase. Ser/Thr-specific protein kinase that dually phosphorylates, and thereby activates, one or more of the MEK enzymes on Ser or Thr residues (Ser-X-X-X-Ser/Thr) within the catalytic core.
ERK/MAPK Pathway
MAPK Mitogen-activated protein kinase subfamily, refers to ERK1 and ERK2, which have the TEY consensus sequence in the catalytic core.
ERK Extracellular signal-regulated protein kinase (or MAPK). Examples are ERK1 (p44) and ERK2 (p42).
Raf MEKK, known to activate the MAPK/ERK pathway. Raf has three isoforms (A-Raf, B-Raf, and C-Raf-1). Raf is activated by several events, including phosphorylation at multiple residues and interaction with p21ras.
MOS Another MEKK enzyme known to activate MAPK/ERKs.
21ras Guanine-nucleotide binding protein (binds GTP and hydrolyzes it to GDP). While GTP is bound, p21ras is in the active conformation. Becomes localized to the membranes as a result of being isoprenylated (attachment of a C15 or C20 lipid molecule) post-translationally.
GRB2 Adaptor proteins containing Src homology 2 and 3 (SH2 and SH3) domains that link protein tyrosine kinases (PTKs) to p21ras, thereby facilitating p21ras-mediated activation of Raf.
SOS Ras guanine-nucleotide exchange factor that catalyzes the exchange of GDP for GTP on p21ras to activate it.
JNK/SAPK Pathway
JNK c-jun amino terminal protein kinase (or SAPK). MAPK superfamily member activated by stress, UV, and inflammatory cytokines. Has TPY consensus sequence in catalytic cores.
c-jun Transcription factor regulated by protein phosphorylation on Ser residues. Forms homo- and heterodimers with jun and fos family members, which enables binding to promoter elements and activation of transcription.
SAPK Stress-activated protein kinase (or JNK).
JNKK Ser/Thr/Tyr specific protein kinase that activates the JNK/SAPK enzymes (or MEK4).
PAK Protein Ser/Thr kinase activated by small GTP-binding proteins like RAC/Cdc42.
RAC Small GTP binding protein that activates PAK and several other effectors.

p38/HOG Pathway

38 Mammalian MAPK superfamily member activated by stress, ultraviolet light, and inflammatory cytokines. Has TGY consensus sequence in catalytic core.

HOG Yeast homolog of mammalian p38 enzyme. Activated by osmotic stress.

Increasingly, aberrantly regulated kinases are being recognized as major causative factors in a number of diseases, particularly proliferative and inflammatory disorders. One of the first oncogenes to be identified in the cancer area was that for the epidermal growth factor receptor kinase (EGFR), overexpression of which is associated with lung, breast, brain, prostate, GI and ovarian cancers.

For example, the constitutive activation of MAP kinase is associated with many cancer cell lines (pancreas, colon, lung, ovary, and kidney) and primary tumors from various human organs (kidney, colon, and lung) (Hoshino et al, *Oncogene*, 18(3):813-22 (January 1999)). In addition, p38 MAP kinase regulates the production of two cytokines, TNF alpha and IL-1, which are associated with the onset and progression of inflammation. In addition to inflammatory diseases such as rheumatoid arthritis, p38 MAP kinase inhibitors may play a future role in the treatment of heart failure, stroke, neurological disease, and other diseases. Thus, MAP kinase inhibitors are useful in treating a wide variety of disease conditions, from cancer to inflammation.

Furthermore, because ERKs are the only substrates so far for MEK1, this tight selectivity, coupled with the pivotal role of the MAP kinase pathway and enhanced expression of its essential components in tumor cells, suggests that the inhibition of the pathway represents an important route to both radio- and chemo-sensitization of tumor cells and a likely target for pharmacological intervention in proliferative diseases.

Sebolt-Leopold et al., *Nat. Med.*, 5(7):810-6 (July 1999), describe an in vitro cascade assay system for identifying small-molecule inhibitors of the MAP kinase (MAPK) pathway. Glutathione-S-transferase (GST)-MEK1 and GST-MAPK fusion proteins were prepared from bacterial cells and used for the sequential phosphorylation of MEK1 to MAPK to MBP (myelin basic protein) in the assay system. The screening led to the discovery of PD 184352 [2-(2-chloro-4-iodo-phenylamino)-N-cyclopropylmethoxy-3,4-difluoro-benzamide] that directly inhibits MEK1. Preliminary data indicate that PD 184352 inhibits the dispersion of epithelial cells (HT-29 colon cancer cells) induced by hepatocyte growth factor/scatter factor, suggesting its use against tumor invasiveness and metastasis. Thus, the MEK inhibitor represents a promising, nontoxic and oral approach to the clinical management of colon cancer.

Exemplary MAP kinase inhibitors include the MAP kinase inhibitors: AG 126, Apigenin, HSP25 Kinase Inhibitor, 5-Iodotubercidin, MAP Kinase Antisense Oligonucleotide, Control MAP Kinase Oligonucleotide, MAP Kinase Cascasde Inhibitor, MAP Kinase Inhibitor Set 1, MAP Kinase Inhibitor Set 2, MEK Inhibitor Set, Olomoucine, Iso Olomoucine, $N^9$ Isopropyl Olomoucine, p38 MAP Kinase Inhibitor, PD 98059, PD 98059 In Solution, PD 169316, SB 202474, SB 202190, SB 202190 In Solution, SB 202190 Hydrochloride, SB 202474 Dihydrochloride, SB 203580, SB 203580 In Solution, SB 203580 Hydrochloride, SB 203580 Sulfone, Ioto-SB 203580, SB 220025, SC 68376, SKF-86002, Tyrphostin AG 126, U0124, U0125, U0126, and ZM 336372. See CalBioChem Catalog at page ixxviii.

Finally, an exemplary p38 MAP kinase inhibitor includes VX-745 (Vertex Pharmaceuticals Inc.). In addition, Tocris Cookson, Inc. (St. Louis, USA) lists various MAP kinase inhibitors at http://www.tocris.com/, given below.

SB 202190

4-[4-(4-Fluorophenyl)-5-(4-pyridinyl)-1H-imidazol-2-yl] phenol. This compound is a highly selective, potent, and cell permeable inhibitor of p38 MAP kinase (SmithKline Beecham, plc). (Jiang et al., *J. Biol. Chem.*, 271:17920 (1996); Frantz et al., Biochemistry, 37:138-46 (1998); Nemoto et al., J. Biol. Chem., 273:16415 (1998); and. Davies et al., *Biochem. J.*, 351:95 (2000).)

Anisomycin (2R,3S,4S)-2-[(4-Methoxyphenyl) methyl]-3,4-pyrrolidinediol 3-acetate. This compound is a protein synthesis inhibitor (blocks translation). It is a potent activator of stress-activated protein kinases (JNK/SAPK) and p38 MAP kinase, and it acts as a potent signaling agonist to selectively elicit homologous desensitisation of immediate early gene induction (c-fos, fosB, c-jun, junB, and junD).

PD 98059

2-(2-Amino-3-methoxyphenyl)-4H-1-benzopyran-4-one. This compound is a specific inhibitor of mitogen-activated protein kinase kinase (MAPKK) (Warner-Lambert Company).

SB 203580

4-[5-(4-Fluorophenyl)-2-[4-(methylsulphonyl)phenyl]-1H-imidazol-4-yl]pyridine. This compound is a highly selective inhibitor of p38 mitogen-activated protein kinase (SmithKline Beecham, plc). It has been shown to inhibit interleukin-2-induced T-cell proliferation, cyclooxygenase-1 and -2, and thromboxane synthase.

SB 203580 hydrochloride

4-[5-(4-Fluorophenyl)-2-[4-(methylsulphonyl)phenyl]-1H-imidazol-4-yl]pyridine. This compound is a water soluble salt of the highly selective inhibitor of p38 mitogen-activated protein kinase. It has been shown to inhibit interleukin-2-induced T-cell proliferation, cyclooxygenase-1 and -2, and thromboxane synthase.

U0126

1,4-Diamino-2,3-dicyano-1,4-bis[2-aminophenylthio] butadiene. This compound is a potent and selective non-competitive inhibitor of MAP kinase kinase.

There is a need in the art for nanoparticulate compositions of MAP kinase inhibitors and methods of making and using such compositions. The present invention satisfies these needs.

SUMMARY OF THE INVENTION

The present invention is directed to nanoparticulate compositions comprising at least one poorly soluble MAP kinase inhibitor and at least one surface stabilizer associated with the surface of the MAP kinase inhibitor.

Another aspect of the invention is directed to pharmaceutical compositions comprising a nanoparticulate MAP kinase inhibitor composition of the invention. The pharmaceutical compositions preferably comprise at least one poorly soluble MAP kinase inhibitor, at least one surface stabilizer associated with the surface of the inhibitor, and a pharmaceutically acceptable carrier, as well as any desired excipients.

This invention further discloses a method of making a nanoparticulate composition having at least one poorly soluble MAP kinase inhibitor and at least one surface stabilizer associated with the surface of the inhibitor. Such a method comprises contacting a poorly soluble nanoparticulate MAP kinase inhibitor with at least one surface stabilizer for a time and under conditions sufficient to provide a MAP kinase inhibitor/surface stabilizer composition. The surface stabilizer can be contacted with the MAP kinase inhibitor either before, during, or after particle size reduction of the MAP kinase inhibitor.

Finally, the present invention is directed to a method of treatment comprising administering to a mammal a therapeutically effective amount of a nanoparticulate MAP kinase inhibitor composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1: Shows the % redispersion in an electrolyte solution, as a function of the concentration of the electrolyte solution, for a spray dried nanoparticulate MAP kinase inhibitor composition.

DETAILED DESCRIPTION OF THE INVENTION

The present invention is directed to the surprising and unexpected discovery that stable nanoparticulate compositions of MAP kinase inhibitors can be made.

Advantages of the MAP kinase inhibitor compositions of the invention include, but are not limited to: (1) faster onset of action; (2) smaller tablet or other solid dosage form size, or smaller volume if in a liquid dosage form; (3) smaller doses of drug required to obtain the same pharmacological effect as compared to conventional microcrystalline forms of the same MAP kinase inhibitor; (4) increased bioavailability as compared to conventional microcrystalline forms of the same MAP kinase inhibitor; (5) substantially similar pharmacokinetic profiles of the MAP kinase inhibitor compositions of the invention when administered in the fed versus the fasted state; (6) bioequivalency of the MAP kinase inhibitor compositions of the invention when administered in the fed versus the fasted state; (7) improved pharmacokinetic profiles; (8) an increased rate of dissolution for the MAP kinase inhibitor compositions of the invention as compared to conventional microcrystalline forms of the same MAP kinase inhibitor; (9) bioadhesive MAP kinase inhibitor compositions; (10) the MAP kinase inhibitor compositions of the invention can be sterile filtered; and (11) the MAP kinase inhibitor compositions of the invention can be used in conjunction with other active agents.

The invention encompasses the MAP kinase inhibitor compositions of the invention formulated or coadministered with one or more non-MAP kinase inhibitor active agents, either conventional (solubilized or microparticulate) or nanoparticulate. Methods of using such combination compositions are also encompassed by the invention.

The present invention is described herein using several definitions, as set forth below and throughout the application.

"About" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein with reference to stable drug particles, 'stable' means that MAP kinase inhibitor particles do not appreciably flocculate or agglomerate due to interparticle attractive forces or otherwise increase in particle size.

"Therapeutically effective amount" as used herein with respect to a drug dosage, shall mean that dosage that provides the specific pharmacological response for which the drug is administered in a significant number of subjects in need of such treatment. It is emphasized that 'therapeutically effective amount,' administered to a particular subject in a particular instance will not always be effective in treating the diseases described herein, even though such dosage is deemed a 'therapeutically effective amount' by those skilled in the art. It is to be further understood that drug dosages are, in particular instances, measured as oral dosages, or with reference to drug levels as measured in blood.

"Conventional active agents or drugs" refers to non-nanoparticulate or solubilized active agents or drugs. Non-nanoparticulate active agents have an effective average particle size of greater than about 2 microns.

A. Preferred Characteristics of the MAP kinase Inhibitor Compositions of the Invention

1. Fast Onset of Activity

The use of conventional formulations of MAP kinase inhibitors is not ideal due to delayed onset of action. This is particularly problematic when the MAP kinase inhibitor is used for treating an inflammatory condition such as arthritis, when fast pain relief is desirable. In contrast, the nanoparticulate MAP kinase inhibitor compositions of the invention exhibit faster therapeutic effects. Moreover, nanoparticulate formulations of MAP kinase inhibitors enable selection of a MAP kinase inhibitor with a long half-life in the blood stream while still providing the subject with a fast-acting compound.

Preferably, following administration the MAP kinase inhibitor compositions of the invention have a $T_{max}$ of less than about 2.5 hours, less than about 2.25 hours, less than about 2 hours, less than about 1.75 hours, less than about 1.5 hours, less than about 1.25 hours, less than about 1.0 hours, less than about 50 minutes, less than about 40 minutes, less than about 30 minutes, less than about 25 minutes, less than about 20 minutes, less than about 15 minutes, or less than about 10 minutes.

2. Increased Bioavailability

The MAP kinase inhibitor compositions of the invention preferably exhibit increased bioavailability, at the same dose of the same MAP kinase inhibitor, and require smaller doses, as compared to prior conventional MAP kinase inhibitor compositions.

Any drug, including MAP kinase inhibitors, can have adverse side effects. Thus, lower doses of MAP kinase inhibitors which can achieve the same or better therapeutic effects as those observed with larger doses of conventional MAP kinase inhibitors are desired. Such lower doses can be realized with the MAP kinase inhibitor compositions of the invention, because the greater bioavailability observed with the nanoparticulate MAP kinase inhibitor compositions as compared to conventional drug formulations means that smaller does of drug are required to obtain the desired therapeutic effect.

3. The Pharmacokinetic Profiles of the MAP kinase Inhibitor Compositions of the Invention are not Substantially Affected by the Fed or Fasted State of the Subject Ingesting the Compositions The invention encompasses a MAP kinase inhibitor composition wherein the pharmacokinetic profile of the MAP kinase inhibitor is not substantially affected by the fed or fasted state of a subject ingesting the composition. This means that there is no substantial difference in the quantity of drug absorbed or the rate of drug absorption when the nanoparticulate MAP kinase inhibitor compositions are administered in the fed versus the fasted state. Thus, the nanoparticulate MAP kinase inhibitor compositions of the invention substantially eliminate the effect of food on the pharmacokinetics of the MAP kinase inhibitor.

Preferably, the difference in absorption of the nanoparticulate MAP kinase inhibitor compositions of the invention, when administered in the fed versus the fasted state, is less than about 100%, less than about 90%, less than about 80%, less than about 70%, less than about 60%, less than about 50%, less than about 40%, less than about 35%, less than about 30%, less than about 25%, less than about 20%, less than about 15%, less than about 10%, less than about 5%, less than about 3%, or essentially no difference.

In addition, preferably the difference in the rate of absorption (i.e., $T_{max}$) of the nanoparticulate MAP kinase inhibitor compositions of the invention, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, less than about 3%, or essentially no difference.

Benefits of a dosage form which substantially eliminates the effect of food include an increase in subject convenience, thereby increasing subject compliance, as the subject does not need to ensure that they are taking a dose either with or without food.

4. Redispersibility Profiles of the MAP kinase Inhibitor Compositions of the Invention An additional feature of the MAP kinase inhibitor compositions of the invention is that the compositions redisperse such that the effective average particle size of the redispersed MAP kinase inhibitor particles is less than about 2 microns. This is significant, as if upon administration the nanoparticulate MAP kinase inhibitor compositions of the invention did not redisperse to a substantially nanoparticulate particle size, then the dosage form may lose the benefits afforded by formulating the MAP kinase inhibitor into a nanoparticulate particle size.

This is because nanoparticulate MAP kinase inhibitor compositions benefit from the small particle size of the MAP kinase inhibitor; if the nanoparticulate MAP kinase inhibitor particles do not redisperse into the small particle sizes upon administration, then "clumps" or agglomerated MAP kinase inhibitor particles are formed, owing to the extremely high surface free energy of the nanoparticulate system and the thermodynamic driving force to achieve an overall reduction in free energy. With the formation of such agglomerated particles, the bioavailability of the dosage form may fall well below that observed with the liquid dispersion form of the nanoparticulate MAP kinase inhibitor composition.

Preferably, the redispersed MAP kinase inhibitor particles of the invention have an effective average particle size of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

5. Bioadhesive MAP kinase Inhibitor Compositions

Bioadhesive MAP kinase inhibitor compositions of the invention comprise at least one cationic surface stabilizer, which are described in more detail below. Bioadhesive formulations of MAP kinase inhibitors exhibit exceptional bioadhesion to biological surfaces, such as mucous. The term bioadhesion refers to any attractive interaction between two biological surfaces or between a biological and a synthetic surface. In the case of bioadhesive nanoparticulate MAP kinase inhibitor compositions, the term bioadhesion is used to describe the adhesion between the nanoparticulate MAP kinase inhibitor compositions and a biological substrate (i.e. gastrointestinal mucin, lung tissue, nasal mucosa, etc.). See e.g., U.S. Pat. No. 6,428,814 for "Bioadhesive Nanoparticulate Compositions Having Cationic Surface Stabilizers," which is specifically incorporated by reference.

The bioadhesive MAP kinase inhibitor compositions of the invention are useful in any situation in which it is desirable to apply the compositions to a biological surface. The bioadhesive MAP kinase inhibitor compositions coat the targeted surface in a continuous and uniform film which is invisible to the naked human eye.

A bioadhesive MAP kinase inhibitor composition slows the transit of the composition, and some MAP kinase inhibitor particles would also most likely adhere to tissue other than the mucous cells and therefore give a prolonged exposure to the MAP kinase inhibitor, thereby increasing absorption and the bioavailability of the administered dosage.

6. Pharmacokinetic Profiles of the MAP kinase Inhibitor Compositions of the Invention The present invention provides compositions of one or more MAP kinase inhibitors having a desirable pharmacokinetic profile when administered to mammalian subjects. Preferably, the $T_{max}$ of an administered dose of a nanoparticulate MAP kinase inhibitor is less than that of a conventional non-nanoparticulate composition of the same MAP kinase inhibitor, administered at the same dosage. In addition, preferably the $C_{max}$ of a nanoparticulate composition of a MAP kinase inhibitor is greater than the $C_{max}$ of a conventional non-nanoparticulate composition of the same MAP kinase inhibitor, administered at the same dosage.

In comparative pharmacokinetic testing with a non-nanoparticulate composition of a MAP kinase inhibitor, a nanoparticulate composition of the same MAP kinase inhibitor, administered at the same dosage, preferably exhibits a $T_{max}$ which is less than about 100%, less than about 90%, less than about 80%, less than about 70%, less than about 60%, less than about 50%, less than about 40%, less than about 30%, less than about 25%, less than about 20%, less than about 15%, or less than about 10% of the $T_{max}$ exhibited by the non-nanoparticulate composition of the MAP kinase inhibitor.

In comparative pharmacokinetic testing with a non-nanoparticulate composition of a MAP kinase inhibitor, a nanoparticulate composition of the same MAP kinase inhibitor, administered at the same dosage, preferably exhibits a $C_{max}$ which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the $C_{max}$ exhibited by the non-nanoparticulate composition of the MAP kinase inhibitor.

The desirable pharmacokinetic profile, as used herein, is the pharmacokinetic profile measured after an initial dose of a MAP kinase inhibitor. The compositions can be formulated in any way as described below.

C. Combination Pharmacokinetic Profile Compositions

In yet another embodiment of the invention, a first MAP kinase inhibitor composition providing a desired pharmacokinetic profile is co-administered, sequentially administered, or combined with at least one other MAP kinase inhibitor composition that generates a desired different pharmacokinetic profile. More than two MAP kinase inhibitor compositions can be co-administered, sequentially administered, or combined. While at least one of the MAP kinase inhibitor compositions has a nanoparticulate particle size, the additional one or more MAP kinase inhibitor compositions can be nanoparticulate, solubilized, or have a conventional microparticulate particle size.

For example, a first MAP kinase inhibitor composition can have a nanoparticulate particle size, conferring a short $T_{max}$ and typically a higher $C_{max}$. This first MAP kinase inhibitor composition can be combined, co-administered, or sequentially administered with a second composition comprising: (1) a different nanoparticulate MAP kinase inhibitor exhibiting slower absorption and, therefore a longer $T_{max}$ and typically a lower $C_{max}$; (2) the same MAP kinase inhibitor having a larger (but still nanoparticulate) particle size, and therefore exhibiting slower absorption, a longer $T_{max}$, and typically a lower $C_{max}$; or (3) a microparticulate MAP kinase inhibitor composition (with the MAP kinase inhibitor being either the same as or different from the MAP kinase inhibitor of the first composition), exhibiting a longer $T_{max}$, and typically a lower $C_{max}$.

The second, third, fourth, etc., MAP kinase inhibitor composition can differ from the first, and from each other, for example: (1) in the identity of the MAP kinase inhibitor; (2) in the effective average particle sizes of each composition; or (3) in the dosage of the MAP kinase inhibitor. MAP kinase inhibitor compositions can produce a different $T_{max}$. Such a combination composition can reduce the dose frequency required.

If the second MAP kinase inhibitor composition has a nanoparticulate particle size, then preferably the MAP kinase inhibitor has at least one surface stabilizer associated with the surface of the drug particles. The one or more surface stabilizers can be the same as or different from the surface stabilizers associated with the surface of the first MAP kinase inhibitor.

Preferably where co-administration of a "fast-acting" formulation and a "longer-lasting" formulation is desired, the two formulations are combined within a single composition, for example a dual-release composition.

D. Compositions

The compositions of the invention comprise at least one poorly soluble MAP kinase inhibitor and at least one surface stabilizer. Surface stabilizers useful herein associate with the surface of the nanoparticulate MAP kinase inhibitor, but do not chemically react with the MAP kinase inhibitor or itself. Preferably, individual molecules of the surface stabilizer are essentially free of intermolecular cross-linkages.

The present invention also includes nanoparticulate MAP kinase inhibitors having at least one surface stabilizer associated with the surface thereof, formulated into compositions together with one or more non-toxic physiologically acceptable carriers, adjuvants, or vehicles, collectively referred to as carriers.

1. MAP Kinase Inhibitor Drug Particles

The nanoparticles of the invention comprise a poorly soluble MAP kinase inhibitor. The MAP kinase inhibitor exists either as a discrete crystalline phase or as an amorphous phase. The crystalline phase differs from a non-crystalline or amorphous phase which results from precipitation techniques, such as those described in EP Patent No. 275,796. By "poorly soluble" it is meant that the MAP kinase inhibitor has a solubility in the liquid dispersion medium of less than about 10 mg/mL, and preferably of less than about 1 mg/mL.

A useful MAP kinase inhibitor according to the invention can inhibit any MAP kinase factor including, but not limited to, MAPK, ERK, MEK, MEKK, ERK1, ERK2, Raf, MOS, p21ras, GRB2, SOS, JNK, c-jun, SAPK, JNKK, PAK, RAC, and p38.

Exemplary MAP kinase inhibitors include, but are not limited to, PD 184352, VX-745, SB 202190, Anisomycin, PD 98059, SB 203580, U0126, AG 126, Apigenin, HSP25 Kinase Inhibitor, 5-Iodotubercidin, MAP Kinase Antisense Oligonucleotide, Control MAP Kinase Oligonucleotide, MAP Kinase Cascasde Inhibitor, MAP Kinase Inhibitor Set 1, MAP Kinase Inhibitor Set 2, MEK Inhibitor Set, Olomoucine, Iso Olomoucine, $N^9$ Isopropyl Olomoucine, p38 MAP Kinase Inhibitor, PD 169316, SB 202474, SB 202190 Hydrochloride, SB 202474 Dihydrochloride, SB 203580 Sulfone, Ioto-SB 203580, SB 220025, SC 68376, SKF-86002, Tyrphostin AG 126, U0124, U0125, and ZM 336372. See CalBioChem Catalog at page ixxviii; http://www.tocris.com/; and http://www.vpharm.com/frame09.html.

2. Non-MAP kinase Inhibitor Active Agents

The nanoparticulate MAP kinase inhibitor compositions of the invention can additionally comprise one or more non-MAP kinase inhibitor active agents, in either a conventional or nanoparticulate particle size. The non-MAP kinase inhibitor active agents can be present in a crystalline phase, an amorphous phase, a semi-crystalline phase, a semi-amorphous phase, or a mixture thereof.

If the non-MAP kinase inhibitor active agent has a nanoparticulate particle size i.e., a particle size of less than about 2 microns, then preferably it will have one or more surface stabilizers associated with the surface of the active agent. In addition, if the active agent has a nanoparticulate particle size, then it is preferably poorly soluble and dispersible in at least one liquid dispersion medium. By "poorly soluble" it is meant that the active agent has a solubility in a liquid dispersion medium of less than about 30 mg/mL, less than about 20 mg/mL, less than about 10 mg/mL, or less than about 1 mg/mL. Useful liquid dispersion mediums include, but are not limited to, water, aqueous salt solutions, safflower oil, and solvents such as ethanol, t-butanol, hexane, and glycol.

Such active agents can be, for example, a therapeutic agent. A therapeutic agent can be a pharmaceutical agent, including biologics such as amino acids, proteins, peptides, and nucleotides. The active agent can be selected from a variety of known classes of drugs, including, for example, amino acids, proteins, peptides, nucleotides, anti-obesity drugs, central nervous system stimulants, carotenoids, corticosteroids, elastase inhibitors, anti-fungals, oncology therapies, antiemetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's *The Extra Pharmacopoeia*, 31st Edition (The Pharmaceutical Press, London, 1996), specifically incorporated by reference. The active agents are commercially available and/or can be prepared by techniques known in the art.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. Dietary supplements and nutraceuticals are also disclosed in *Physicians' Desk Reference for Nutritional Supplements*, 1 st Ed. (2001) and *The Physicians' Desk Reference for Herbal Medicines*, 1 st Ed. (2001), both of which are also incorporated by reference. A nutraceutical or dietary supplement, also known as phytochemicals or functional foods, is generally any one of a class of dietary supplements, vitamins, minerals, herbs, or healing foods that have medical or pharmaceutical effects on the body.

Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., arginine, iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bioengineered foods genetically engineered to have a desired property, also known as "pharmafoods."

The compound to be administered in combination with a nanoparticulate MAP kinase inhibitor composition of the invention can be formulated separately from the MAP kinase inhibitor composition or co-formulated with the MAP kinase inhibitor composition. Where a MAP kinase inhibitor composition is co-formulated with a second active agent, the second active agent can be formulated in any suitable manner, such as immediate-release, rapid-onset, sustained-release, or dual-release form.

3. Surface Stabilizers

Useful surface stabilizers, which are known in the art and described in the '684 patent, are believed to include those which associate with the surface of the MAP kinase inhibitor but do not chemically bond to or interact with the MAP kinase inhibitor. The surface stabilizer is associated with the surface of the MAP kinase inhibitor in an amount sufficient to maintain the MAP kinase inhibitor particles at an effective average particle size of less than about 2000 nm. Furthermore, the individually adsorbed molecules of the surface stabilizer are preferably essentially free of intermolecular cross-linkages. Two or more surface stabilizers can be employed in the compositions and methods of the invention.

Suitable surface stabilizers can preferably be selected from known organic and inorganic pharmaceutical excipients. Such excipients include various polymers, low molecular weight oligomers, natural products, and surfactants. Surface stabilizers include nonionic, cationic, zwitterionic, and ionic surfactants.

Representative examples of surface stabilizers include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (DOSS) (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL-40® (Croda, Inc.); and SA9OHCO, which is $C_{18}H_{37}CH_2(CON(CH_3)—CH_2(CHOH)_4(CH_20H)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl (C$_{12-18}$)dimethylbenzyl ammonium chloride, N-alkyl (C$_{14-18}$) dimethyl-benzyl ammonium chloride, N-tetradecylidmethylbenzyl ammonium chloride monohydrate, dimethyl didecyl ammonium chloride, N-alkyl and (C$_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl(C$_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C$_{12}$, C$_{15}$, C$_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™ (polyquaternium 10; Buckman Laboratories, TN), tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ (quaternized ammonium salt polymers) and ALKAQUAT™ (benzalkonium chloride) (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula NR$_1$R$_2$R$_3$R$_4{}^{(+)}$. For compounds of the formula NR$_1$R$_2$R$_3$R$_4{}^{(+)}$:

(i) none of R$_1$-R$_4$ are CH$_3$;
(ii) one of R$_1$-R$_4$ is CH$_3$;
(iii) three of R$_1$-R$_4$ are CH$_3$;
(iv) all of R$_1$-R$_4$ are CH$_3$;
(v) two of R$_1$-R$_4$ are CH$_3$, one of R$_1$-R$_4$ is C$_6$H$_5$CH$_2$, and one of R$_1$-R$_4$ is an alkyl chain of seven carbon atoms or less;
(vi) two of R$_1$-R$_4$ are CH$_3$, one of R$_1$-R$_4$ is C$_6$H$_5$CH$_2$, and one of R$_1$-R$_4$ is an alkyl chain of nineteen carbon atoms or more;
(vii) two of R$_1$-R$_4$ are CH$_3$ and one of R$_1$-R$_4$ is the group C$_6$H$_5$(CH$_2$)$_n$, where n>1;
(viii) two of R$_1$-R$_4$ are CH$_3$, one of R$_1$-R$_4$ is C$_6$H$_5$CH$_2$, and one of R$_1$-R$_4$ comprises at least one heteroatom;
(ix) two of R$_1$-R$_4$ are CH$_3$, one of R$_1$-R$_4$ is C$_6$H$_5$CH$_2$, and one of R$_1$-R$_4$ comprises at least one halogen;
(x) two of R$_1$-R$_4$ are CH$_3$, one of R$_1$-R$_4$ is C$_6$H$_5$CH$_2$, and one of R$_1$-R$_4$ comprises at least one cyclic fragment;
(xi) two of R$_1$-R$_4$ are CH$_3$ and one of R$_1$-R$_4$ is a phenyl ring; or
(xii) two of R$_1$-R$_4$ are CH$_3$ and two of R$_1$-R$_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

4. Nanoparticulate MAP kinase Inhibitor/Surface Stabilizer Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The nanoparticulate MAP kinase inhibitor compositions of the invention have an effective average particle size of less than about 2 microns. By "an effective average particle size of less than about 2 microns" it is meant that at least 50% of the MAP kinase inhibitor particles have a particle size of less than about 2 microns when measured by the above techniques.

In other embodiments, the effective average particle size of the nanoparticulate MAP kinase inhibitor particles is less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, or less than about 50 nm, when measured by the above techniques.

In yet other embodiments of the invention, at least about 70%, about 90%, about 95%, or about 99% of the particles have a particle size less than the effective average particle size, i.e., less than about 2000 nm, less than about 1900 nm, less than about 1800 nm, etc.

If the nanoparticulate MAP kinase inhibitor composition additionally comprises one or more non-MAP kinase inhibitor nanoparticulate active agents, then such active agents have an effective average particle size of less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2 microns" it is meant that at least 50% of the MAP kinase inhibitor or active agent particles have a particle size of less than about 2 microns, by weight, when measured by the above techniques. In other embodiments of the invention, at least about 70%, about 90%, about 95%, or about 99% of the particles have a particle size which is less than the effective average, i.e., less than about 2000 nm, less than about 1900 nm, less than about 1800 nm, etc.

If the nanoparticulate MAP kinase inhibitor is combined with a conventional or microparticulate MAP kinase inhibitor or non-MAP kinase inhibitor composition, then such a conventional composition is either solubilized or has an effective average particle size of greater than about 2 microns. By "an effective average particle size of greater than about 2 microns" it is meant that at least 50% of the conventional MAP kinase inhibitor or active agent particles have a particle size of greater than about 2 microns, by weight, when measured by the above-noted techniques. In other embodiments of the invention, at least about 70%, about 90%, about 95%, or about 99% of the conventional MAP kinase inhibitor or active agent particles have a particle size greater than about 2 microns.

5. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

6. Concentration of Nanoparticulate MAP kinase inhibitor and Stabilizer

The relative amount of MAP kinase inhibitor and one or more surface stabilizers can vary widely. The optimal amount of the surface stabilizers can depend, for example, upon the particular MAP kinase inhibitor selected, the hydrophilic lipophilic balance (HLB), melting point, water solubility of the surface stabilizer, and the surface tension of water solutions of the stabilizer, etc.

The concentration of the at least one MAP kinase inhibitor can vary from about 99.5% to about 0.001%, from about 95% to about 0.1%, or from about 90% to about 0.5%, by weight, based on the total combined weight of the at least one MAP kinase inhibitor and at least one surface stabilizer, not including other excipients.

The concentration of the one or more surface stabilizers can vary from about 0.5% to about 99.999%, from about 5.0% to about 99.9%, or from about 10% to about 99.5%, by weight, based on the total combined dry weight of the at least one MAP kinase inhibitor and at least one surface stabilizer, not including other excipients.

E. Methods of Making Nanoparticulate Formulations

The nanoparticulate MAP kinase inhibitor compositions can be made using, for example, milling, precipitation, or homogenization techniques. Exemplary methods of making nanoparticulate compositions are described in the '684 patent. Methods of making nanoparticulate compositions are also described in U.S. Pat. No. 5,518,187, for "Method of Grinding Pharmaceutical Substances;" U.S. Pat. No. 5,718, 388, for "Continuous Method of Grinding Pharmaceutical Substances;" U.S. Pat. No. 5,862,999, for "Method of Grinding Pharmaceutical Substances;" U.S. Pat. No. 5,665,331, for "Co-Microprecipitation of Nanoparticulate Pharmaceutical Agents with Crystal Growth Modifiers;" U.S. Pat. No. 5,662,883, for "Co-Microprecipitation of Nanoparticulate Pharmaceutical Agents with Crystal Growth Modifiers;" U.S. Pat. No. 5,560,932, for "Microprecipitation of Nanoparticulate Pharmaceutical Agents;" U.S. Pat. No. 5,543,133, for "Process of Preparing X-Ray Contrast Compositions Containing Nanoparticles;" U.S. Pat. No. 5,534,270, for "Method of Preparing Stable Drug Nanoparticles;" U.S. Pat. No. 5,510,118, for "Process of Preparing Therapeutic Compositions Containing Nanoparticles;" and U.S. Pat. No. 5,470,583, for "Method of Preparing Nanoparticle Compositions Containing Charged Phospholipids to Reduce Aggregation," all of which are specifically incorporated by reference.

One or more non-MAP kinase inhibitor active agents can be reduced in size at the same time as the MAP kinase inhibitor, to produce a nanoparticulate MAP kinase inhibitor and nanoparticulate non-MAP kinase inhibitor active agent composition. A non-MAP kinase inhibitor active agent, which is either conventional or nanoparticulate sized, can also be added to the nanoparticulate MAP kinase inhibitor composition after particle size reduction.

In yet another embodiment of the invention, nanoparticulate MAP kinase inhibitor compositions of the invention can be made in which the formulation comprises multiple nanoparticulate MAP kinase inhibitor compositions, each of which has a different effective average particle size. Such a composition can be made by preparing the individual nanoparticulate MAP kinase inhibitor compositions using, for example, milling, precipitation, or homogenization techniques, followed by combining the different compositions to prepare a single dosage form.

The nanoparticulate MAP kinase inhibitor compositions can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

1. Milling to Obtain Nanoparticulate Dispersions

Milling of aqueous MAP kinase inhibitors to obtain a nanoparticulate dispersion comprises dispersing MAP kinase inhibitor particles in a liquid dispersion medium in which the MAP kinase inhibitor is poorly soluble, followed by applying mechanical means in the presence of grinding media to reduce the particle size of the MAP kinase inhibitor to the desired effective average particle size. The MAP kinase inhibitor particles can be reduced in size in the presence of at least one surface stabilizer. Alternatively, the MAP kinase inhibitor particles can be contacted with one or more surface stabilizers either before or after attrition. Other compounds, such as a diluent, can be added to the MAP kinase inhibitor/surface stabilizer composition either before, during, or after the size reduction process. Dispersions can be manufactured continuously or in a batch mode.

2. Precipitation to Obtain Nanoparticulate MAP kinase Inhibitor Compositions

Another method of forming the desired nanoparticulate MAP kinase inhibitor composition is by microprecipitation. This is a method of preparing stable dispersions of MAP kinase inhibitors in the presence of one or more surface stabilizers and one or more colloid stability enhancing surface active agents free of any trace toxic solvents or solubilized heavy metal impurities. Such a method comprises, for example: (1) dissolving at least one MAP kinase inhibitor in a suitable solvent; (2) adding the formulation from step (1) to a solution comprising at least one surface stabilizer to form a clear solution; and (3) precipitating the formulation from step (2) using an appropriate non-solvent. The method can be followed by removal of any formed salt, if present, by dialysis or diafiltration and concentration of the dispersion by conventional means. Dispersions can be manufactured continuously or in a batch mode.

3. Homogenization to Obtain Nanoparticulate MAP kinase Inhibitor Compositions

Exemplary homogenization methods of preparing nanoparticulate compositions are described in U.S. Pat. No. 5,510,118, for "Process of Preparing Therapeutic Compositions Containing Nanoparticles." Such a method comprises dispersing MAP kinase inhibitor particles in a liquid dispersion medium, followed by subjecting the dispersion to homogenization to reduce the particle size of the MAP kinase inhibitor to the desired effective average particle size. The MAP kinase inhibitor particles can be reduced in size in the presence of at least one surface stabilizer. Alternatively, the MAP kinase inhibitor particles can be contacted with one or more surface stabilizers either before or after attrition. Other compounds, such as a diluent, can be added to the MAP kinase inhibitor/surface stabilizer composition either before, during, or after the size reduction process. Dispersions can be manufactured continuously or in a batch mode.

F. Methods of Using Nanoparticulate MAP kinase Inhibitor Formulations Comprising One or More Surface Stabilizers MAP kinase inhibitors can be useful in treating inflammatory diseases. For example, lowering circulatory levels of proinflammatory cytokines IL-1b and TNF-alpha has recently been shown to have clinical benefits in the treatment of various inflammatory diseases, such as rheumatoid arthritis and Crohn's disease. The p38 MAP kinase is known to regulate signal transduction in response to environmental stress, and provides a way to stop the production of IL-1b and TNF-alpha early in the cascade. See http://www.albmolecular.com/features/tekreps/vol05/no10/.

The nanoparticulate compositions of the present invention can be administered to humans and animals in any pharmaceutically acceptable manner, including, but not limited to orally, pulmonary, rectally, ocularly, colonicly, parenterally (e.g., intravenous, intramuscular, or subcutaneous), intracisternally, intravaginally, intraperitoneally, locally (e.g., powders, ointments, or drops), buccally, nasal, and topically. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propylene glycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate MAP kinase inhibitor compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the nanoparticulate MAP kinase inhibitor is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the MAP kinase inhibitor, the liquid dosage forms may comprise inert diluents commonly used in the art, such as water or other solvents, solubilizing agents, and emulsifiers. Besides such inert diluents, the composition can also include adjuvants, such as wetting agents, emulsifying and suspending agents, sweetening, flavoring, and perfuming agents.

One of ordinary skill will appreciate that effective amounts of a MAP kinase inhibitor can be determined empirically and can be employed in pure form or, where such forms exist, in pharmaceutically acceptable salt, ester, or prodrug form. Actual dosage levels of MAP kinase inhibitor in the nanoparticulate compositions of the invention may be varied to obtain an amount of active ingredient that is effective to obtain a desired therapeutic response for a particular composition and method of administration. The selected dosage level therefore depends upon the desired therapeutic effect, the route of administration, the potency of the MAP kinase inhibitor, the desired duration of treatment, and other factors.

The daily dose may be administered in single or multiple doses. It will be understood, however, that the specific dose level for any particular patient will depend upon a variety of factors including the body weight, general health, sex, diet, time and route of administration, potency of the administered MAP kinase inhibitor, rates of absorption and excretion, combination with other drugs and the severity of the particular disease being treated, and like factors well known in the medical arts.

The following example is given to illustrate the present invention. It should be understood, however, that the invention is not to be limited to the specific conditions or details described in this example. Throughout the specification, any and all references to a publicly available document, including a U.S. patent, are specifically incorporated by reference.

Example 1

The purpose of this example was to prepare nanoparticulate composition of VX-745, which is a MAP kinase inhibitor.

In 2001, Vertex obtained clinical proof-of-concept in a Phase II trial of its oral p38 MAP kinase inhibitor, VX-745, in rheumatoid arthritis. Vertex researchers solved the structure of p38 MAP kinase in 1996, and following intensive modeling and computational chemistry efforts, advanced VX-745 as a lead candidate in 1998. Vertex initiated the first clinical trial of VX-745 in March 1999, and has conducted an exploratory trial of VX-745 in patients with rheumatoid arthritis. In January 2000, Vertex commenced a dose-ranging Phase II clinical trial with VX-745 in patients with rheumatoid arthritis. See http://www.vpharm.com/frame09.1 html.

The structure of VX-745 is given below (http://www.alb-molecular.com/features/tekreps/vol05/no10/):

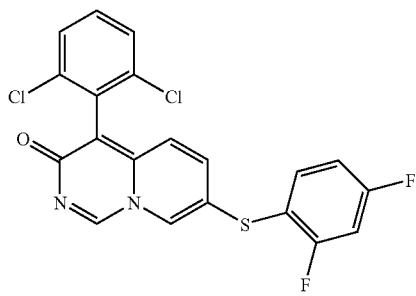

A mixture of 10% (w/w) of VX-745 and 2% (w/w) Pluronic® F108 (which is a triblock copolymer of polyethylene oxide and polypropylene oxide) was milled for 6 hrs at 10° C. using a DYNO®-Mill equipped with a 300 cc recirculation chamber using 500 µm milling media of type PolyMill®-500.

The mean particle size (volume statistics) of the milled VX-745 dispersion was 231 nm, with 50%<218 nm, 90%<351 nm, and 95%<420 nm, measured using a Horiba LA-910 Laser Scattering Particle Size Distribution Analyzer (Horiba Instruments, Irvine, Calif.).

This example demonstrates the successful preparation of a stable nanoparticulate composition of a MAP kinase inhibitor.

Example 2

The purpose of this example was to demonstrate sterile filtration of a nanoparticulate dispersion of VX-745.

The nanoparticulate formulation prepared in Example 1 was further milled as follows: In three separate portions, 90 g of nanoparticulate 10% (w/w) VX-745 and 2% (w/w) Pluronic® F108 was charged into the 150 cc batch chamber of a DYNO®-Mill and each milled for 2 hr using 50 µm polymeric media of the type SDy-20. The three harvested portions were then combined.

The mean particle size of the milled VX-745 dispersion (volume statistics) was 98 nm, with 50%<90 nm, 90%<141 nm, and 95%<200 nm, measured using a Horiba LA-910 Laser Scattering Particle Size Distribution Analyzer (Horiba Instruments, Irvine, Calif.). The dispersion was filtered first through a 1 µm filter (Whatman PolyCap™ 75 HD) followed by a 0.2 µm sterilizing grade filter (Pall/Gelman Supor® SpiralCap).

This example demonstrates the successful preparation of a stable nanoparticulate composition of a MAP kinase inhibitor that can be sterilized by 0.2 µm filtration.

Example 3

The purpose of this example was to prepare a nanoparticulate dispersion of Compound A, which is a MAP kinase inhibitor.

A mixture of 5% (w/w) of Compound A, 2% (w/w) HPC-SL (hydroxypropylcellulose), and 0.02% (w/w) DOSS was roller milled for 45 hours in a 100 mL glass bottle using 0.8 mm YTZ (yttria-doped zirconia) ceramic milling media.

The mean particle size (volume statistics) of the milled Compound A dispersion was 220 nm, with 50%<213 nm, 90%<304 nm, and 95%<336 nm, measured using a Horiba LA-910 Laser Scattering Particle Size Distribution Analyzer (Horiba Instruments, Irvine, Calif.).

This example demonstrates the successful preparation of a stable nanoparticulate composition of a MAP kinase inhibitor.

Example 4

The purpose of this example was to prepare a nanoparticulate dispersion of Compound B, which is a MAP kinase inhibitor.

A mixture of 5% (w/w) of Compound B and 1.25% (w/w) Pluronic® F108 was roller milled for 45 hours in a 100 mL glass bottle using 0.8 mm YTZ (yttria-doped zirconia) ceramic milling media.

The mean particle size (volume statistics) of the milled Compound B dispersion was 141 nm, with 50%<130 nm, 90%<196 nm, and 95%<230 nm, measured using a Horiba LA-910 Laser Scattering Particle Size Distribution Analyzer (Horiba Instruments, Irvine, Calif.).

This example demonstrates the successful preparation of a stable nanoparticulate composition of a MAP kinase inhibitor.

Exhibit 5

The purpose of this example was to prepare nanoparticulate composition of the MAP kinase inhibitor VX-745.

A mixture of 20% (w/w) of VX-745, 4% (w/w) HPC-SL, and 0.12% (w/w) SLS (sodium lauryl sulfate) was milled for 5.5 hrs using a DYNO®-Mill equipped with a 600 cc recirculation chamber using 500 μm milling media of type PolyMill™-500. The coolant temperature for the mill chamber was 0° C.

The mean particle size (volume statistics) of the milled VX-745 dispersion was 96 nm, with 50%<90 nm, 90%<145 nm, and 95%<170 nm, measured using a Horiba LA-910 Laser Scattering Particle Size Distribution Analyzer (Horiba Instruments, Irvine, Calif.).

This example demonstrates the successful preparation of a stable nanoparticulate composition of a MAP kinase inhibitor.

Exhibit 6

The purpose of this example was to prepare nanoparticulate composition of the MAP kinase inhibitor VX-745.

A mixture of 30% (w/w) of VX-745, 6% (w/w) PVP K29/32 (povidone), and 0.3% DOSS (w/w) (docusate sodium) was milled for 3.25 hrs using a DYNO®-Mill equipped with a 150 cc batch chamber using 500 μm milling media of type PolyMillT™-500. The coolant temperature for the mill chamber was 10° C.

The mean particle size (volume statistics) of the milled VX-745 dispersion was 98 nm, with 50%<91 nm, 90%<148 nm, and 95%<169 nm, measured using a Horiba LA-910 Laser Scattering Particle Size Distribution Analyzer (Horiba Instruments, Irvine, Calif.).

This example demonstrates the successful preparation of a stable nanoparticulate composition of a MAP kinase inhibitor.

Example 7

The purpose of this example was to prepare nanoparticulate composition of the MAP kinase inhibitor VX-745.

A mixture of 10% (w/w) of VX-745 and 2% (w/w) HPC-SL was milled for 2.5 hrs using a DYNO®-Mill equipped with a 150 cc batch chamber using 500 μm milling media of type PolyMill™-500. The coolant temperature for the mill chamber was 10° C.

The mean particle size (volume statistics) of the milled VX-745 dispersion was 97 nm, with 50%<87 nm, 90%<150 nm, and 95%<198 nm, measured using a Horiba LA-910 Laser Scattering Particle Size Distribution Analyzer (Horiba Instruments, Irvine, Calif.

This example demonstrates the successful preparation of a stable nanoparticulate composition of a MAP kinase inhibitor.

Exhibit 8

The purpose of this example was to prepare a solid dose of a nanoparticulate composition of VX-745.

The nanoparticulate MAP kinase inhibitor dispersion of Example 7 was diluted to 5% (w/w) VX-745 and combined with lactose and sodium lauryl sulfate to give a final composition with the proportions 1 part VX-745:1 part lactose:0.06 parts SLS. This composition was spray dried in a Büchi Mini Spray Dryer (Model B-191; Büchi, Switzerland). The inlet air temperature was 120° C., aspirator setting=100%, pump setting=10%. The outlet temperature ranged from 50-55° C. A dry powder of the nanoparticulate VX-745 dispersion was thus obtained. The dry powder can be utilized in an aerosol composition, or it can be compressed and tableted to form a solid dose for oral or other suitable administration.

This example demonstrates the successful preparation of a solid dose form of a nanoparticulate composition of a MAP kinase inhibitor.

Exhibit 9

The purpose of this example was to test the redispersion properties of the solid dose form of VX-745 in an aqueous medium, as prepared in Example 8.

The spray dried powder of Example 8 was redispersed in water and the particle size distribution of the reconstituted material was measured. The mean particle size (volume statistics) of the reconstituted VX-745 dispersion was 101 nm, with 50%<92 nm, 90%<161 nm, and 95%<198 nm, measured using a Horiba LA-910 Laser Scattering Particle Size Distribution Analyzer (Horiba Instruments, Irvine, Calif.).

The results show that the solid dose nanoparticulate MAP kinase inhibitor composition showed excellent redispersion in the aqueous medium.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A nanoparticulate mitogen-activated protein (MAP) kinase inhibitor composition comprising:

(a) particles of a poorly soluble MAP kinase inhibitor or a salt thereof having an effective average particle size of less than about 2000 nm; and (b) associated with the surface thereof at least one surface stabilizer, wherein the at least one surface stabilizer is selected from the group consisting of a polymeric stabilizer, poloxamer, hydroxypropylcellulose, docusate sodium, sodium lauryl sulfate, and povidone.

2. The composition of claim 1, wherein the at least one MAP kinase inhibitor is selected from the group consisting of PD 184352, VX-745, SB 202190, Anisomycin, PD 98059, SB 203580, U0126, AG 126, Apigenin, HSP25 Kinase Inhibitor, 5-Iodotubercidin, MAP Kinase Antisense Oligonucleotide, Control MAP Kinase Oligonucleotide, MAP Kinase Cascasde Inhibitor, MAP Kinase Inhibitor Set 1, MAP Kinase Inhibitor Set 2, MEK Inhibitor Set, Olomoucine, Iso Olomoucine, $N^9$ Isopropyl Olomoucine, p38 MAP Kinase Inhibitor, PD 169316, SB 202474, SB 202190 Hydrochloride, SB 202474 Dihydrochloride, SB 203580 Sulfone, Ioto-SB 203580, SB 220025, SC 68376, SKF-86002, Tyrphostin AG 126, U0124, U0125, and ZM 336372.

3. The composition of claim 1, wherein the MAP kinase inhibitor is selected from the group consisting of a crystalline phase, an amorphous phase, a semi-crystalline phase, a semi-amorphous phase, and mixtures thereof.

4. The composition of claim 1, wherein the effective average particle size of the nanoparticulate MAP kinase inhibitor is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm.

5. The composition of claim 1, wherein the composition is formulated:

(a) for administration selected from the group consisting of oral, pulmonary, rectal, opthalmic, colonic, parenteral, intracisternal, intravaginal, intraperitoneal, local, buccal, nasal, and topical administration;

(b) into a dosage form selected from the group consisting of liquid dispersions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations; or (c) a combination of (a) and (b).

6. The composition of claim 1, wherein the composition further comprises one or more pharmaceutically acceptable excipients, carriers, or a combination thereof.

7. The composition of claim 1, wherein:

(a) the MAP kinase inhibitor is present in an amount selected from the group consisting of from about 99.5% to about 0.001%, from about 95% to about 0.1%, and from about 90% to about 0.5%, by weight, based on the total combined weight of the MAP kinase inhibitor and at least one surface stabilizer, not including other excipients;

(b) the at least one surface stabilizer is present in an amount selected from the group consisting of from about 0.5% to about 99.999%, from about 5.0% to about 99.9%, and from about 10% to about 99.5%, by weight, based on the total combined weight of the at least one MAP kinase inhibitor and at least one surface stabilizer, not including other excipients; or (c) a combination of (a) and (b).

8. The composition of claim 1, comprising at least two surface stabilizers.

9. The composition of claim 8, wherein the second surface stabilizer is selected from the group consisting of an anionic surface stabilizer, a cationic surface stabilizer, an ionic surface stabilizer, and a zwitterionic surface stabilizer.

10. The composition of claim 8, wherein the second surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oils, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, $C_{18}H_{37}CH_2C(O)N(CH_3)$—$CH_2(CHOH)_4(CH_2OH)_2$, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-vitamin A, PEG-vitamin E, random copolymers of vinyl acetate and vinyl pyrrolidone, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl ($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, and cationic guar.

11. The composition of claim 10, wherein the composition is bioadhesive.

12. The composition of claim 1, wherein the composition comprises more than one MAP kinase inhibitor.

13. The composition of claim 12, wherein at least one MAP kinase inhibitor has an effective average particle size which is greater than about 2 microns.

14. The composition of claim 1, additionally comprising at least one nanoparticulate MAP kinase inhibitor composition having an effective average particle size of less than about 2 microns, wherein said additional nanoparticulate MAP kinase inhibitor composition has an effective average particle size which is different than the particle size of the nanoparticulate MAP kinase inhibitor composition of claim 1.

15. The composition of claim 1, additionally comprising at least one non-MAP kinase inhibitor active agent.

16. The composition of claim 15, wherein said active agent is selected from the group consisting of amino acids, proteins, peptides, nucleotides, anti-obesity drugs, nutraceuticals, dietary supplements, central nervous symptom stimulants, carotenoids, corticosteroids, elastase inhibitors, anti-fungals, alkylxanthine, oncology therapies, anti-emetics, analgesics, opioids, antipyretics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, alpha-adrenergic receptor blocking agents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, anti-allergic agents, stimulants, anoretics, sympathomimetics, thyroid agents, vasodilators, vasomodulator, xanthines, Mu receptor antagonists, Kappa receptor antagonists, non-narcotic analgesics, monoamine uptake inhibitors, adenosine regulating agents, cannabinoid derivatives, Substance P antagonists, neurokinin-1 receptor antagonists, and sodium channel blockers.

17. The composition of claim 16, wherein said nutraceutical is selected from the group consisting of lutein, folic acid, fatty acids, fruit extracts, vegetable extracts, vitamin supplements, mineral supplements, phosphatidylserine, lipoic acid, melatonin, glucosamine/chondroitin, Aloe Vera, Guggul, glutamine, amino acids, green tea, lycopene, whole foods, food additives, herbs, phytonutrients, antioxidants, flavonoid constituents of fruits, evening primrose oil, flax seeds, fish oils, marine animal oils, and probiotics.

18. The composition of claim 15, wherein:
(a) at least one non-MAP kinase inhibitor active agent has an effective average particle size of less than about 2 microns; or
(b) at least one non-MAP kinase inhibitor active agent has an effective average particle size of greater than about 2 microns.

19. The composition of claim 1, wherein upon administration the composition redisperses such that the MAP kinase inhibitor particles have a particle size selected from the group consisting of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

20. The composition of claim 19, wherein the composition is a solid dosage form.

21. The composition of claim 1, wherein the composition has been sterile filtered.

22. The composition of claim 1, wherein:
(a) the composition does not produce significantly different absorption levels when administered under fed as compared to fasting conditions;
(b) the composition does not produce significantly different rates of absorption ($T_{max}$) when administered under fed as compared to fasting conditions; or
(c) a combination of (a) and (b).

23. The composition of claim 1, wherein:
(a) the difference in absorption of the nanoparticulate MAP kinase inhibitor composition of the invention, when administered in the fed versus the fasted state, is selected from the group consisting of less than about 100%, less than about 90%, less than about 80%, less than about 70%, less than about 60%, less than about 50%, less than about 40%, less than about 35%, less than about 30%, less than about 25%, less than about 20%, less than about 15%, less than about 10%, less than about 5%, and less than about 3%; or
(b) the difference in the $T_{max}$ for the nanoparticulate MAP kinase inhibitor composition of the invention, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, and less than about 3%; or
(c) a combination of (a) and (b).

24. The composition of claim 1, wherein:
(a) upon administration the $T_{max}$ is less than that of a conventional non-nanoparticulate composition of the same MAP kinase inhibitor, administered at the same dosage;
(b) upon administration the $C_{max}$ of the composition is greater than the $C_{max}$ of a conventional non-nanoparticulate composition of the same MAP kinase inhibitor, administered at the same dosage; or
(c) a combination of (a) and (b).

25. The composition of claim 1, wherein in comparative pharmacokinetic testing with a non-nanoparticulate composition of the same MAP kinase inhibitor, administered at the same dosage, the nanoparticulate composition exhibits a $T_{max}$ selected from the group consisting of less than about 100%, less than about 90%, less than about 80%, less than about 70%, less than about 60%, less than about 50%, less than about 40%, less than about 30%, less than about 25%, less than about 20%, less than about 15%, and less than about 10% of the $T_{max}$ exhibited by the non-nanoparticulate composition of the MAP kinase inhibitor.

26. The composition of claim 1, wherein following administration the composition has a $T_{max}$ selected from the group consisting of less than about 2.5 hours, less than about 2.25 hours, less than about 2 hours, less than about 1.75 hours, less than about 1.5 hours, less than about 1.25 hours, less than about 1.0 hours, less than about 50 minutes, less than about 40 minutes, less than about 30 minutes, less than about 25 minutes, less than about 20 minutes, less than about 15 minutes, and less than about 10 minutes.

27. The composition of claim 1, wherein in comparative pharmacokinetic testing with a non-nanoparticulate composition of the same MAP kinase inhibitor, administered at the same dosage, the nanoparticulate composition exhibits a $C_{max}$ selected from the group consisting of greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, and greater than about 150% than the $C_{max}$ exhibited by the non-nanoparticulate composition of the MAP kinase inhibitor.

28. A method of making a mitogen-activated protein (MAP) kinase inhibitor composition comprising contacting particles of at least one poorly soluble MAP kinase inhibitor with at least one surface stabilizer for a time and under conditions sufficient to provide a MAP kinase inhibitor composition having an effective average particle size of less than about 2 microns, wherein the at least one surface stabilizer is selected from the group consisting of a polymeric stabilizer, poloxamer, hydroxypropylcellulose, docusate sodium, sodium lauryl sulfate, and povidone.

29. A method of treating a subject in need with a mitogen-activated protein (MAP) kinase inhibitor composition comprising administering to the subject an effective amount of a MAP kinase inhibitor composition comprising:
(a) particles of a poorly soluble MAP kinase inhibitor or a salt thereof having an effective average particle size of less than about 2000 nm; and
(b) associated with the surface thereof at least one surface stabilizer, wherein the at least one surface stabilizer is selected from the group consisting of a polymeric stabilizer, poloxamer, hydroxypropylcellulose, docusate sodium, sodium lauryl sulfate, and povidone.

30. The method of claim 29, wherein the at least one MAP kinase inhibitor is selected from the group consisting of PD 184352, VX-745, SB 202190, Anisomycin, PD 98059, SB 203580, U0126, AG 126, Apigenin, HSP25 Kinase Inhibitor, 5-Iodotubercidin, MAP Kinase Antisense Oligonucleotide, Control MAP Kinase Oligonucleotide, MAP Kinase Cascasde Inhibitor, MAP Kinase Inhibitor Set 1, MAP Kinase Inhibitor Set 2, MEK Inhibitor Set, Olomoucine, Iso Olomoucine, $N^9$ Isopropyl Olomoucine, p38 MAP Kinase Inhibitor, PD 169316, SB 202474, SB 202190 Hydrochloride, SB 202474 Dihydrochloride, SB 203580 Sulfone, Ioto-SB 203580, SB 220025, SC 68376, SKF-86002, Tyrphostin AG 126, U0124, U0125, and ZM 336372.

31. The method of claim 29, wherein the effective average particle size of the nanoparticulate MAP kinase inhibitor particles is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm.

32. The method of claim 29, wherein the method is used to treat an condition where a selective MAP kinase inhibitor is indicated.

33. The method of claim 29, wherein the method is used to treat an inflammatory disease.

34. The method of claim 29, wherein the method is used to treat a condition selected from the group consisting of rheumatoid arthritis and Crohn's disease.

35. The method of claim 29, wherein the subject is a human.

* * * * *